United States Patent [19]

Springer et al.

[11] Patent Number: 6,005,002
[45] Date of Patent: *Dec. 21, 1999

[54] NITROGEN MUSTARD PRODRUGS WITH NOVEL LIPOPHILIC PROTECTING GROUPS, AND PROCESSES FOR THEIR PRODUCTION

[75] Inventors: Caroline Joy Springer; Ion Niculescu-Duvaz, both of Sutton, United Kingdom

[73] Assignee: Cancer Research Campaign Technology Limited, London, United Kingdom

[ * ] Notice: This patent is subject to a terminal disclaimer.

[21] Appl. No.: 08/875,099

[22] PCT Filed: Jan. 19, 1996

[86] PCT No.: PCT/GB96/00112

§ 371 Date: Jul. 16, 1997

§ 102(e) Date: Jul. 16, 1997

[87] PCT Pub. No.: WO96/22277

PCT Pub. Date: Jul. 25, 1996

[30] Foreign Application Priority Data

Jan. 19, 1995 [GB] United Kingdom .................. 9501052

[51] Int. Cl.$^6$ ......................... A01N 47/10; C07C 205/06; C07C 271/50
[52] U.S. Cl. .......................... 514/483; 514/490; 560/21; 560/24; 560/25; 560/133
[58] Field of Search .................................. 560/13, 34, 43, 560/21, 24, 25, 133; 514/483, 490

[56] References Cited

FOREIGN PATENT DOCUMENTS

| | | |
|---|---|---|
| 0 540 263 | 5/1993 | European Pat. Off. . |
| 1463764 | 11/1966 | France . |
| WO88/07378 | 10/1988 | WIPO . |
| WO94/02450 | 2/1994 | WIPO . |
| WO95/02420 | 1/1995 | WIPO . |
| WO95/03830 | 2/1995 | WIPO . |

OTHER PUBLICATIONS

Anthony B. Mauger et al., "Self–Immolative Prodrugs: Candidates for Antibody–Directed Enzyme Prodrug Therapy in Conjunction with a Nitroreductase Enzyme", *Journal of Medical Chemistry*, vol. 37, No. 21, pp. 3452–3458 (Oct. 14, 1994).

*Primary Examiner*—Gary Geist
*Assistant Examiner*—Brian J. Davis
*Attorney, Agent, or Firm*—Venable

[57] ABSTRACT

The invention provides compounds of formula (I) and (II) wherein X and Y are independently chlorine, bromine, iodine, a mesyl group $CH_3SO_3$ or a tosyl group $OSO_2$phenyl (wherein phenyl is optionally substituted by 1, 2, 3, 4 or 5 substituents independently selected from $C_{1-4}$alkyl, halogen, cyano or nitro; $R^1$ and $R^2$ are independently 1 to 4 optional substituents; $Z^1$ and $Z^2$ are each independently —O— or —NH—; $R^3$ is hydrogen, t-butyl or allyl; $Z^3$ is a hydrocarbyl group such as carboxyethyl, optionally containing heteroatoms, and physiologically acceptable derivatives thereof. The compounds can be converted in situ into nitrogen mustard agents by the actions of enzymes such as carboxypeptidase or nitroreductase and are useful for the treatment of cancer.

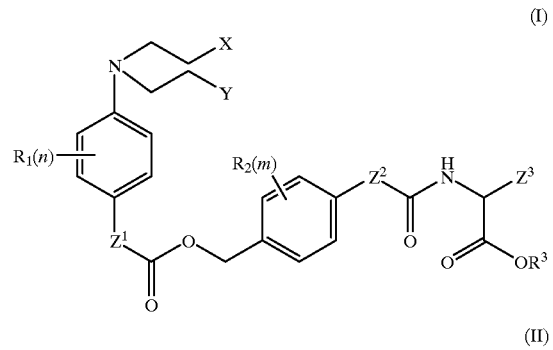

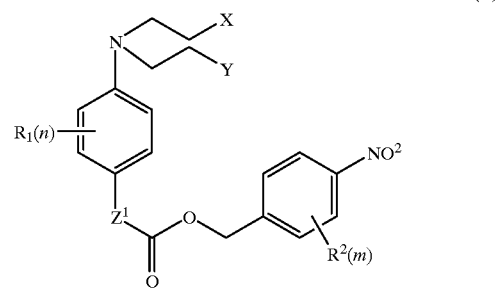

10 Claims, 3 Drawing Sheets

NITROGEN MUSTARD PRODRUGS WITH NOVEL LIPOPHILIC PROTECTING GROUPS, AND PROCESSES FOR THEIR PRODUCTION

The present invention relates to prodrugs and their use in the treatment of disease, including cancers.

The use of prodrugs represents a clinically very valuable concept in cancer therapy since. particularly where the prodrug is to be converted to an anti-tumour agent under the influence of an enzyme that is linkable to a monoclonal antibody that will bind to a tumour associated antigen, the combination of such a prodrug with such an enzyme monoclonal/antibody conjugate represents a very powerful clinical agent. This approach to cancer therapy, often referred to as "antibody directed enzyme/prodrug therapy" (ADEPT) is disclosed in WO88/07378.

More recently. a similar approach ("GDEPT", Gene-Directed Enzyme Prodrug Therapy) has been proposed where in place of an antibody/enzyme conjugates tumour cells are targeted with a viral vector carrying a gene encoding an enzyme capable of activating a prodrug. The gene may be transcriptionally regulated by tumour specific promoter or enhancer sequences. The viral vector enters tumour cells and expresses the enzyme, in order that a prodrug is converted to an active drug only in the vicinity of the tumour cells (Huber et al. Proc. Natl. Acad. Sci. USA (1991) 88, 8039). The enzvme may be targeted to particular subcellular locations or expressed at the cell surface.

The present invention provides novel prodrugs which contain protecting groups which are more lipophilic than compounds of the prior art such as those disclosed in WO88/07378. Accordingly, the present invention provides compounds of the formula (I):

wherein X and Y are independently chlorine, bromine, iodine, a mesyl group $CH_3 SO_3$ or a tosyl group $OSO_2$phenyl (wherein phenyl is optionally substituted by 1, 2, 3, 4 or 5 substituents independently selected from $C_{1-4}$alkyl, halogen, cyano or nitro;

n is an integer from 0 to 4 and each group $R^1$, which may be the same or different when n is greater than 1, is fluorine, chlorine, bromine, iodine, hydroxy, mercapto, amino, nitro, $C_{1-4}$alkyl optionally containing one double bond or one triple bond, $C_{1-4}$ alkoxy, —$CONR^7R^8$ (wherein $R^7$ and $R^8$ are as defined below), —$NH(C_{1-4}$-alkyl), —$N(C_{1-4}$alkyl)$_2$ or $C_{2-5}$ alkanoyl; or when n is 2 or more and two groups $R^1$ are on adjacent positions on the phenylene ring, 2 adjacent $R^1$ groups together represent a) C4 alkylene optionally having one double bond;
b) C3 alkylene; or
c) —CH=CH—CH=CH—, —CH=CH—CH$_2$— or —CH$_2$—CH=CH— each optionally substituted with 1, 2, 3 or 4 substituents said substituents each independently selected from the group consisting of $C_{1-4}$ alkyl, $C_{1-4}$ alkoxy, halogen, cyano, nitro, $C_{2-5}$ alkanoyl and —CONR7R8 (wherein R7 and R8 are as defined below);

m is an integer from 0 to 4 and $R^2$, which may be the same or different when m is greater than 1, is fluorine, chlorine, bromine, iodine, hydroxy, mercapto, amino, nitro, $C_{1-4}$ alkyl optionally containing one double bond or one triple bond, $C_{1-4}$ alkoxy, —$CONR^7R^8$ (wherein $R^7$ and $R^8$ are as defmed below), —$NH(C_{1-4}$-alkyl), —$N(C_{1-4}$-alkyl)$_2$ and $C_{2-5}$ alkanoyl; or when n is 2 or more and two groups $R^1$ are on adjacent positions on the phenylene ring, 2 adjacent $R^1$ groups together represent a) C4 alkylene optionally having one double bond;
b) C3 alkylene; or
c) —CH=CH—CH=CH—, —CH=CH—CH$_2$— or —CH$_2$—CH=CH— each optionally substituted with 1, 2, 3 or 4 substituents said substituents each independently selected from the group consisting of $C_{1-4}$ alkyl, $C_{1-4}$ alkoxy, halogen, cyano, nitro, $C_{2-5}$ alkanoyl and —CONR7R8 (wherein R7 and R8 are as defined below);

$Z^1$ and $Z^2$ are each independently —O— or —NH—;

$R^3$ is hydrogen, t-butyl or allyl;

$Z^1$ is a group —V—W where V is —$CH_2$—T— in which T is —$CH_2$—, —O—, —S—, —(SO)— or —(SO$_2$)— (provided that when V has sulphur or oxygen as its second atom, W is other than —COOH) and said group V optionally further carrying one or two substituents Q1 and/or Q2 on carbon; wherein $Q^1$ and $Q^2$ each independently represents $C_{1-4}$ alkyl or halogen; or, when Q1 and Q2 are bonded to adjacent carbon atoms, $Q^1$ and $Q^2$ together may additionally represent a $C_3$-$C_4$ alkylene radical optionally substituted with 1, 2, 3 or 4 substituents independently selected from the group consisting of $C_{1-4}$ alkyl and halogen and W represents
(1) COOH,
(2) —(C=O)—O—R6 wherein R6 represents a $C_{1-6}$ alkyl, $C_{3-6}$ cycloalkyl or aryl (as defined in 3 below) group;
(3) —(C=O)—NR7R8 wherein R7 and R8 each independently represent hydrogen or a C1–6 alkyl, C3–6 cycloalkyl, aryl, heteroaryl linked to N via carbon or C7–9 aralkyl group wherein
aryl is phenyl;
heteroaryl is a 5 or 6 membered ring containing 1 to 3 heteroatoms selected from the group consisting of nitrogen and sulphur;
the aryl moiety pet se, the heteroaryl moiety and the aryl moiety of the aralkyl group may be substituted on carbon with 1–4 substituents selected from the group consisting of —COOH, —OH, —NH$_2$, —CH$_2$—NH$_2$, —(CH2)$_{1-4}$—COOH, tetrazol-5-yl and -SO$_3$H and the alkyl moiety may optionally carry a methyl group;
(4) —SO$_2$NHR9 wherein R9 is as defined for R7 but may additionally represent —CF$_3$, —CH$_2$CF$_3$ or aryl as defined above;
(5) SO$_3$R10 in which R10 represents H, $C_{1-6}$ alkyl or $C_{3-6}$ cycloalkyl,
(6) PO$_3$R10R10 (wherein the R10 radicals, which may be the same or different, are as herein defined)
(7) a tetrazl-5-yl group;

(8) —CONH—SO₂R11 in which R11 represents
  (a) C₃₋₇ cycloalkyl;
  (b) C₁₋₆-alkyl optionally substituted with substituents selected from the group consisting of aryl as defined below, C₁₋₄-alkyl, CF₃ or halogen; and
  (c) perfluoro-C₁₋₆ alkyl; wherein
    aryl is phenyl or phenyl having 1–5 substituents wherein the substituents are selected from the group consisting of halogen, —NO₂, —CF₃, C₁₋₄ alkyl, C₁₋₄ alkoxy, —NH₂, —NHCOCH₃, —CONH₂, —OCH₂COOH, —NH(C₁₋₄alkyl), —N(C₁₋₄-alkyl)₂, —NHCOOC₁₋₄ alkyl, —OH, —COOH, —CN and —COOC₁₋₄ alkyl; and
(9) —M-Het wherein M represents S, SO or SO₂ and Het represents a 5 or 6 membered heterocyclic aromatic ring linked to M via a carbon atom of the aromatic ring, said aromatic ring containing 1, 2, 3 or 4 heteroatoms selected from the group consisting of O, N and S said aromatic ring optionally being substituted on carbon atoms of the ring with 1, 2, 3 or 4 substituients selected from the group consisting of —OH, —SH, —CN, —CF₃, NH₂ and halogen;
and physiologically acceptable derivatives of the compound of formula (I).

These prodrugs can be activated at the site of a tumour by a carboxypeptidase enzyme, for example, CPG2 as disclosed in WO88/07378 or WO94/02450. The carboxypeptidase enzyme may be delivered to the site of a tumour by a GDEPT system as described in the prior art. A carboxypeptidase enzyme is capable of removing the glutamic acid or glutamic acid derivative moiety (which are preferably in the L-configuration) of compounds of the formula (I). While not wishing to be bound by any one particular theory, it is believed the removal of the glutamic acid moiety from the compounds produces an unstable internmediate compound which undergoes self-irmmolation to remove the 4-amino or 4-hydroxyl-benzylic system (situated between the groups $Z^1$ and $Z^2$) thus leading to the release of the alkylating nitrogen mustard drug.

CPG enzyme is available from Sigma Chemical Company, Fancy Road, Poole, Dorset, U.K. CPG enzyme was described in: Goldman, P. and Levy, C. C., PNAS USA, 58: 1299–1306 (1967) and in: Levy, C. C. and Goldman P., J. Biol. Chem., 242: 2933–2938 (1967). Carboxypeptidase G3 enzyme has been described in Yasuda, N. et al., Biosci. Biotech. Biochem., 56: 1536–1540 (1992). Carboxypeptidase G2 enzyme has also been described in European Patent 121 352.

Large scale purification of CPG2 from Pseudomonas RS-16 was described in Sherwood et al. (1985), Fur. J. Biochem., 148, 447–453.

CPG2 many also be obtained by recombinant techniques The nucleotide coding sequence for CPG2 has been published by Minton, N. P. et al., Gene, 31 (1984), 31–38. Expression of the coding sequence has been reported in *E.coli* (Chambers, S. P. et al., Appl. Microbiol, Biotechnol. (1988), 29, 572–578) and in *Saccharomyces cerevisiae* (Clarke, L. E. et al., J. Gen Microbiol, (1985) 131, 897–904). Total gene synthesis has been described by M. Edwards in Am. Biotech. Lab (1987), 5. 38–44.

The present invention further provides nitrogen mustard prodrugs of the formula (II):

(II)

wherein X, Y, $R^1$, n, $Z^1$, $R^2$ and m are as defined for comnpounds of the formula (I), and physiologically acceptable derivatives thereof.

These prodrugs can be activated at the site of a tumour by a nitroreductase enzyme, for example, as disclosed in WO93/08288. The nitroreductase enzyme may be delivered to the site of a tumour by a GDEPT system as described in the prior art.

Physiologically acceptable derivatives of said prodrugs of formulae (I) and (II) include salts, esters and salts of esters. Esters include carboxylic acid esters in which the non-carbonyl moiety of the ester grouping is selected from straight or branched chain C₁₋₆alkyl, (methyl, n-propl, n-butyl or t-butyl); or C₃₋₆cyclic alkyl (e.g. cyclohexyl). Salts include physiologically acceptable base salts, eg derived from an appropriate base, such as alkali metal (e.g. sodium), alkaline earth metal (e.g. magnesium) salts, anmmonium and NR₄ (wherein R is C₁₋₄ alkyl) salts. Other salts include acid addition salts, including the hydrochloride and acetate salts.

Preferred values of X and Y are independently chloro, iodo and mesyl.

Preferably, n either is zero or is 1 or 2 and the group(s) $R^1$ are independently fluorine, chlorine, bromine, iodine or C₁₋₄ alkyl. Similarly, it is preferred that either m is zero or is 1 or 2 and the group(s) $R^2$ are independently fluorine, chlorine, bromine, iodine or C₁₋₄ alkyl.

$R^3$ is preferably hydrogen.

$Z^1$ is preferably a group —V—W where V is —CH₂CH₂— and W is a group —COOH, —(C=O)—OR6 where $R^6$ is as defined above, or —(C=O)—NR⁷R⁸ where $R^7$ and $R^8$ are independently hydrogen or C₁₋₆ alkyl.

Preferred compounds of the formula (I) are those in which $Z^1$, $Z^2$, n and m are as defined above, and:
  X and Y are independently selected from chloro, iodo or mesyl;
  each phenylene group which may be optionally substituted by $R^1$ and $R^2$ is unsubstituted or if either is substituted, the group(s) $R^1$ and/or $R^2$ are independently selected from fluorine, chlorine, bromine, iodine or C₁₋₄ alkyl;
  $R^3$ is hydrogen; and
  $Z^3$ is a group —CH₂CH₂—COOH.

Compounds of the formula (I) which are especially preferred are those in which X and Y independently represent iodo or chloro; n and m are both zero;
  $R_3$ represents hydrogen; $Z_1$ and $Z_2$ each independently represent —NH— or —O—; and $Z_3$ represents CH₂CH₂COOH.

Preferred compounds of the formula (II) are those in which $Z^1$ is —O— or —NH—, X and Y are The independently selected from iodo and mesyl, each phenylene group which may be optionally substituted by $R^1$ and $R^2$ is unsubstituted or if either is substituted, the group(s) $R^1$ and/or $R^2$ are independently selected from fluorine, chlorine, bromine, iodine or $C_{1-4}$ alkyl, most preferably fluorine. and in which case n and/or m are 1 or 2.

Compounds of the formula (II) which are especially preferred are those in which X represents iodo; n represents zero; $Z^1$ represents —O— or —NH—; $R_2$ represents hydrogen or fluorine: and m represents an integer from 1 or 2.

The invention further provides pharmaceutical formulations. Such formulations comprise a compound of formula (I) or (II) together with one or more pharmaceutically acceptable carriers or diluents.

Pharmaceutically acceptable carriers or diluents include those used in formulations suitable for oral or parenteral (e.g. intramuscular or intravenous) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both. and then, if necessary, shaping the product.

For example, formulations suitable for parenteral administration include aiqueous and non-aqueous sterile injection solutions which may contain anti-oxidants, buffers, bacteriostatis and solutes which render the formulation isotonic with the blood of the intended recipient; and aqueous and non-aqueous sterile suspensions which may include suspending agents and thickening agents, and liposomes or other microparticulate systems which are designed to target the polypeptide to blood components or one or more organs.

Suitable liposomes include, for example, those comprising the positively charged lipid (N[1-(2,3-dioleyloxy) propyl]-N,N,N-triethylammonium (DOTMA), those comprising dioleoyl-phosphatidylethanolamine (DOPE), and those comprising 3β[N-(n',N'-dimethylaminoethane)-carbamoyl]cholesterol (DC-Chol).

In GDEPT the prodrug will usually be administered following the administration of a delivery system containing the gene encoding the enzyme. This includes administration of a modified virus encoding an enzyme. Typically, the virus will be administered to the patient and then the uptake of the virus by infected cells monitored, for example by recovery and analysis of a biopsy sample of targeted tissue.

A wide range of viral delivery systems for gene therapy are known in the art. For example EP-A-415 731 describes molecular chimeras comprising a promoter which may be activated in a tumour cell is operably linked to a heterologotis gene encoding an enzvme capable of converting a prodrug into a cytotoxic agent. Such molecular chimeras may be used to express carboxypeptidase or nitroreductase in tumour cells, in order to activate prodrugs of the invention. EP-A-415 731 describes incorporation of such molecular chimeras into viral vectors, e.g. adenoviral or retroviral vectors. Such viral vectors may also be adaptel for utilization in the present invention.

Other recombinant viral vector delivery systems are described in WO91/02805. WO92/14829. WO93/10814, WO94/21792, WO95/07994 and WO95/14091 the disclosures of which are incorporated herein by reference. Methods for producing vector delivery systems based on the above-mentioned disclosures may be used to deliver vectors encoding nitroreductase or carboxypeptidase to target cells.

The exact dosage regime for GDEPT will, of course, need to be determined by individual clinicians for individual patients and this, in turn, will be controlled by the exact nature of the prodrug and the cytotoxic agent to be released from the prodrug but some general guidance can be given. Chemotherapy of this type will normally involve parenteral administration of both the prodrug and the enzyme or a vector encoding the enzyme and administration by the intravenous route is frequently found to be the most practical.

In GDEPT systems. the amount of vector delivered will be such as to provide an effective cellular concentration of enzyme so that the prodrug may be activated in sufficient concentrations at the site of a tumour to achieve a therapeutic effect, e.g. reduction in the tumour size. This may be determined by clinical trials which involve administering a range of trial doses to a patient and measuring the degree of infection or transfection of a target cell or tumour. The amount of prodrug required will be similar to or greater than that for ADEPT systems of the type mentioned above. For example, suitable dose of prodrugs in such systems are described in Bagshawe et al, 1991 in Antibody, Immunoconjugates and Radio-Pharmaceuticals I, 915–922. Such doses eg. from 5 to 2000 mg/m$^2$ (eg about 200 mg/m$^2$ per dose (eg every one or two days or weekly) of prodrugs of the invention may be used, although doses outside this range may be used at the discretion of the physician.

The present invention also provides a system for use in the control of neoplasia in a human or animal subject comprising a vector or other delivery system capable of selectively infecting tumour cells in said subject, said vector carrying a DNA or RNA sequence encoding an enzyme, in associaition with a prodrug of formula (I) or (II) capable of being converted to a nitrogen mustard compound by the action of said enzyme.

The present invention extends to a method of treating neoplasia in a human or animal subject requiring such treatment which comprises administering to the host an effective amount of a prodrug of the invention and a modified virus, said modified virus capable of selectively infecting tumour cells in said subject, said virus carrying a DNA or RNA sequence encoding an enzyme capable of converting said prodrug to an active nitrogen mustard compound.

The present invention also extends to a method of treating neoplasia in a human or animal subject requiring such treatmnent which comprises administering to the host an effective amount of a prodrug of the invention and a non viral vector system, said non-viral vector system capable of being selectively introduced into tumour cells in said subject, said vector system carrying a DNA or RNA sequence encoding an enzyme capable of converting said prodrug to an active nitrogen mustard operably linked to a promoter effective in expressing said enzyme in said cells.

Vectors capable of selectively infecting tumour cells are known in the art. By "selectively infecting" it is meant that the vector, for example a modified virus, will primarily infect tumour cells and that the proportion of non-tumour cells infected is such that the damage to tumor non-tumour cells by administration of the prodrug will be acceptably low, given the nature of the disease being treated. Ultimately, this will be determined by the physician.

It will also be understood that the DNA or RNA sequence encoding an enzyme carried by the virus will be linked to suitable expression control signals such that expression of the enzyme will occur in the targeted tumour cells.

Non-viral vector systems will be capable of being selectively introduced into tumour cells utilizing methods such as those mentioned above, e.g. calcium phosphate co-precipitation, microinjection, liposomes, direct DNA uptake, and receptor-mediated DNA transfer (Morgan & French Anderson, Annu. Rev. Biochem., 1993,62;191).

Prodrugs of the present invention may also be used as reagents in in vitro systems to test the activity of candidate enznmes which may be incorporated into GDEPT systems.

For example, a tumour cell mat be infected or transfected in vitro by a vector containing an enzyme. The enzyme will be one which is, or suspected to be, capable of converting a prodrug of the invention into an active drug. The prodrug is then added to the culture and the amount of cell killing or inhibition of cell growth is measured (for example by using a vital stain to record the number of viable cells or by replating a sample of the culture to count the number of viable cells). This model system may also be used to test the toxicity, activity or selectivity of compounds of the present invention against a range of tumour cell types suitable tumour cells for use in these model systems include ovarian, colon, glioma, breast, small cell and non-small cell lung cancer cells. and melanomas.

The invention further provides processes for the production of compounds of formulae (I) and (II). Thus the invention provides a process for the production of a compound of formula (I) as defined above which comprises reacting a compound of the formula (III)

(III)

in which X, Y, $R^1$ and n are as defined for formula (I) and $Z^4$ is —O— or —NH— with a compound of formula (IV)

(IV)

in which $R^2$, m, $Z^2$, $Z^3$ and $R^3$ are as defined above, and Q is a leaving group. The reaction may be performed in an aprotic solvent and in the presence of a base. The invention also provides a process for the production of compounds of the formula (II) which comprises reacting a compound of formula (III) as defined above with a 4-nitrobenzyl chloroformate optionally substituted with from 1 to 4 group(s) $R^2$ as defined above.

The invention further provides compounds of the formula (IV);

(IV)

in which $R^2$, m, $Z^2$, $R^3$ and $Z^3$ are as defined above for compounds of the formula (I), and Q is a leaving group, with the proviso that when $R^2$ is fluorine, chlorine, bromine, iodine, hydroxy, mercapto, amino, nitro, $C_{1-4}$ alkyl, $C_{1-4}$ haloalkyl, $C_{1-4}$ alkoxy, $C_{1-4}$ haloalkoxy, $C_{2-4}$ alkenyl, $C_{2-4}$ alkynyl, and $C_{2-4}$ haloalkenyl. $R^3$ is hydrogen or a $C_{1-6}$ alkyl group, and $Z^3$ is a group —$CH_2CH_2COOX^{10}$ where $X^{10}$ is hydrogen or a C1-6alkyl group, then Q is not a N-succinimidyloxy group. These compounds are useful as linkers which may be attached to active cytotoxic compounds to provide prodrugs of said compounds with increased lipophilicity. The compounds of formula (IV) may be linked to such cytoxic compounds via free —OH or —$NH_2$ groups on such compounds, using methods and reactions described below, or modified using routine experimentation.

Such protected cytotoxic compounds may be useful in GDEPT methods, or in vitro assays used to study such methods.

Compounds of the invention may be made using reactions and methods known per se in the art of chemistry. The following methods are of particular use, and are further illustrated by reference to the Examples where indicated. Such reference does not limit the general reaction schemes to those compounds alone. The schemes may be used for other compounds of the invention:

A: Compounds of Formula (I) Where $Z^1$ is —O—:

(i) Compounds of formula (I) in which $Z^1$=—O— and $Z^2$=—NH—, may be prepared by the reaction of a nitrogen mustard of formula (III)

(III)

wherein X, Y, R$^1$ and n are as defined above and Z$^4$ is —O— with a linker of formula (IV)

(IV)

where R$^2$, m, R$^3$ and Z$^3$ are as defined above, Z$^2$=—NH— and Q is a leaving group.

Preferred leaving groups Q include a succinimidyloxy group, a 4-nitrophenyloxy group, a pentafluorophenyloxy group and a tetrachoroethyloxy CH(Cl)CCl$_3$ group. The reaction may be carried out in aprotic solvents in the presence of a base, for example THF and triethylamine or acetonitrile and basic resins (Example 1).

(ii) Compounds of the formula (III) may be made starting from 4-nitrophenol optionally, substituted with the group(s) R$^1$$_{(n)}$ (as defined above). The phenolic group is protected as an adamantanyloxycarbonyl-derivative (by reacting the starting materials with adamantanyl-fluoroformate and triethylamine in THF at rt). The protected 4-nitrophenyl carbonate is reduced to the corresponding amine by hydrogen transfer in ethanol using ammonium formate and Pd/C 10% as catalyst at rt. The amine is then hydroxyethylated with ethylene oxide in AcOH at 20° C. and then reacted to the desired nitrogen mustard. Reference may be made to EP-A-433 360 or EP-A-490970 for suitable conditions. The compounds may be purified by column chromatozraphy. Deprotection to remove the adamantyl group may be carried out in trifluoroacetic acid.

(iii) Alternatively, the nitrogen mustard of formula (III) may be activated as a chloroformate by treatment with phosgene or triphosgene in an aprotic solvent and triethylamine followed by coupling with a compound of formula (V):

(V)

where R$^2$, m, Z$^2$, R$^3$ and Z$^3$ are as defined above. This may be carried out in THF or other aprotic solvents in the present of a base (for example triethylamine or pyridine).

(iv) A further alternative route of synthesis of compounds of the formula (I) in which Z$^1$ is —O— involves direct coupling of 4-nitrophenol optionally substituted with the group(s) R$^1$$_{(n)}$ (as defined above) with the compound of the formula (IV) or by reaction of the said optionally substituted 4-nitrophenol compound chloroformate with the compound of formula (VI), in which Z$^2$ is —NH— (see below) followed in each case by the reaction described above to convert the nitro group, via an amine, to a mustard group.

(v). A way of obtaining compound (I) where Z$^1$=—O— and Z$^2$=—O— is from nitrogen mustard (III) where Z$^4$=—O—, by transforming it to the trimethylsilyl derivative. The silylated phenol is then coupled with a compound of formula (V) where Z$^2$=—O—. Compound (V) is first activated as the fluoroformate with KF, phosgene and crown ether at −78° C., in an aprotic solvent (see Example 2). prior to reaction with silyated phenol.

B: Compounds of Formula (I) Where Z$^1$ is —NH—:

(i) Compounds of the formula (I) in which Z$^1$ is —NH— may be made by reaction of a compound of formula (III) in which Z$^4$ is —NH— with a linker of the formula (IV) in aprotic solvents and in the presence of a base. Compounds of the formula (III) in which Z$^4$ is —NH— may be made from a 1-halo4-nitrophenyl compound, optionally substituted with the group(s) R$^1$$_{(n)}$ (as defined above). This is converted to the corresponding 1-bis-hydroxyethylamino4-nitrophenvl compound by reaction with diethanolamine with heat and the resulting product purified by column chromatography. The corresponding 4-nitro nitrogen mustard may be made by for example mesylation using mesyl chloride in pyridine and subsequent reaction to other halo mustards, e.g. bromo or iodo mustards if required. The 4-nitro group may be reduced by hydrogen transfer in ethanol using ammonium formate and a Pd/C 10% catalyst at 20° C.

(ii) Alternatively the 1-bis-hydroxyethylamino-4-nitrophenyl compound mentioned above can be reduced using ammonium formate and Pd/C 10% as catalyst in ethanol at 20° C. to provide the corresponding phenylenediamino derivative. This derivative can be converted into the corresponding 4-amino nitrogen mustard as described in the above paragraph. e.g. initially by reaction with mesyl chloride.

(iii) In an alternative route, the nitrogen mustard (III) Z$^4$=—NH— may be activated as an isocyanate by treatment with phosgene or triphosgene in an aprotic solvent followed by coupling with a compound of formula V where R$^2$, m, Z$^2$, R$^3$ and Z$^3$ are as defined above. The coupling may be carried out in aprotic solvents and in the presence of a catalyst, for example dibutyltin dilaurate (see Examples 3 and 4).

C: Compounds of Formula (II):

(i) Compounds of the formula (II) may be obtained by coupling nitrogen inustard phenol compounds described in section A(ii) above with 4-nitrobenzyl choloroformate optionally substituted with the group(s) $R^2_{(m)}$ (as defined above) in the presence or absence of triethylamine at 20° C. This is used to provide compounds of formula (II) in which $Z^1$ is —O—

(ii) Alternatively aniline nitrogen mustards as described in section B(ii) above may be used with the chloroformate as described in section C(i) above. This is used to provide compounds of the formula (II) in which $Z^1$ is —NH—.

D: Compounds of the Formula (IV) in Which $Z^2$ is —NH—:

(i) Compounds of the formula (IV) in which $Z^2$ is —NH— may be made from a 4-nitro benzylic alcohol optionally substituted with the group(s) $R^2_{(m)}$ (as defined above). The hydroxyl function is protected as a pyanyl- or t-butyl-dimethylsilyl (TBDMSi)-ether by treatment at 20° C. with 3,4-2H-dihydropyran and pyridinium-p-toluensulfonate (PPTS) in an aprotic solvent or with TBDMSi chloride and imidazole in dimethylformamide (DMAT), respectively (Example 5). The intermediate thus obtained is reduced to the corresponding amninle by hydrogen transfer in ethanol using ammonium formate and Pd/C 10% as catalyst at 20° C. This amine is converted to a glutamyl ester intermediate of formula (VI) (Example 6):

(VI)

where $R^2$, m, $R^3$ and $Z^3$ are as defined above, $Z^2$ is —NH— and Pr is the pyanyl- or t-butyl-dimethylsilyl (TBDMSi)-ether protecting group. This may be done by treating the amine with triphosgene and triethylamine in toluene at 60° C. to provide the corresponding isocyante. which is coupled with a glutamate derivative of formula $R^3O$—C(O)—CH(NH$_2$)—$Z^3$ where $R^3$ and Z are as defined above. Alternatively the corresponding glutamy-isocynate obtained from the corresponding glutamate by treatment with triphosgene and triethylamine in toluene at -78° C. may be reacted with the amine in a one pot procedure (Example 7). Glutamate derivatives of formula $R^3O$—C(O)—CH(NH$_2$)—$Z^3$ may be obtained by reference to WO94/02450. Where necessary or desired, the group $Z^3$ may be converted to another group $Z^3$ using routine chemistry known per se following production of the compound of formula (VI). or after reaction of that to the compound of formula (I).

(ii) The compound of formula (VI) is deprotected to remove the TBDMSi or pyranyl groups by treatment with mild acidic media (AcOH. THF and H$_2$O or PPTS. EtOH. 55° C.) (Example 8). This yields a compound of formula (VI) in which Pr is hydrogen. Compounds of the formila IV) in which Q is a leaving group may be prepared using standard reactions. known in the art (Example 8).

(iii) Where Q is a succinimidyl group the compound of formula (VI) where Pr is hydrogen may be treated with disuccinimidyl-carbonate and triethylamine in acetonitrile. Where a 4-nitrophenyl carbonate group is desired treatment with 4-nitrophenyl chloroformate and triethylamine in THF may be used (Example 9). A pentafluorophenyl carbonate may be added by in situ phosgenation of pentafluorophenol followed by coupling to the linker of formula (VI) in which Pr is hydrogen.

(iv) The compound of formula (VI) in which Pr is hydrogen may be obtained directly by coupling of the 4-aminobenzylic alcohol with glutamyl-isocyanate in aprotic solvents (Example 10).

E: Compounds of the Formula (IV) in Which $Z^2$ is —O—:

(i) The starting materials for the linkers possessing a carbamic bond are unsubstituted or substituted (with the grup(s) $R^2_{(m)}$ (as defined above)) 4-hydroxy-benzylic alcohols. These type of linkers may require an extra electron withdrawing group on the aromatic nucleus in order to undergo 1,4-elimination. The 4-hydroxy group is specifically protected as an acetate by treating the starting material with acetyl-v-triazolo-[4,5-b]pyridine, and 1N NaOH in THF at 20° C. The alcohol function of the acetate is further protected as pyranyl- or TBDMSi-ether by the procedures described in section D above. The acetate function is then deprotected to restore the 4-hydroxy group in NaHCO$_3$ aq. MeOH at 20° C. The resulting phenol compounds are reacted in a one pot procedure with a protected glutamyl-isocyanate as described in section D(i) above. This yields a compound of the formula of (VI) as shown above in which $Z^2$ is —O— and Pr is the pyanyl- or t-butyl-dimethylsilyl (TBDMSi)-ether protecting group.

(ii) Deprotection of this compound yields a compound of the formula (VI) in which Pr is hydrogen. This may be converted to compounds of the formula (IV) by methods analogous to those described in section D (iii) above.

(iii) An alternative procedure starts from 4-hydroxy-benzaldehyde which is protected with 1,3-propane-dithiol in the presence of BF$_3$Et$_2$O, at room temperature to give the 4[2'-(1',3'-S,S-dithianyl)]phenol. The coupling of the protected phenol with glutamyl isocyanate in toluene in the presence of Et$_3$N provides the di-tert-butyl, O—{4-[2'(1',3'-S,S-dithianyl)]phenyl}oxycarbonyl-L-glutamate. The deprotection of this intermediate to the corresponding aldehyde, is carried out with Hg(ClO$_4$)$_2$ in THF at room temperature. The reduction of the aldehyde with a reducing agent like sodium cyano-borohvdryde yields the desired compound of formula (VI) in which Pr is hydrogen and $Z^2$ is —O— (Example 11).

(iv) Another procedure to obtain the deprotected aldehyde is by direct coupling of 4-hydroxy-benzaldehyde with the glutamyl-isocyanate (Example 12).

(v) An alternative route to the compound of formula (VI) in which $Z^2$ is —O— and Pr is hydrogen is by direct coupling of the 4-hydroxy-benzylic alcohol, as potassium phenolate obtained from the starting material and potassium tert-butoxyde in the presence of crown ether) with the corresponding glutamyl-isocyanate in aprotic solvents (Example 13).

(vi) The compound of formula (IV) in which $Z^2$ is —O— and Q is a leaving group may be prepared using standard reactions known in the art. For example where Q is a 4-nitrophenyl carbonate group the compound of formula (VI) where Pr is hydrogen may be treated with 4-nitrophenyl chloroformate and triethylamine in THF (Example 14).

F: Alternative Synthesis of Compounds of Formula (IV):

Compounds of the formula (IV) in which Q is hydrogen, fluoro, chloro, bromo or —O—(N-succinimide) may also be obtained by reference to WO95/03830 published on Feb. 9, 1995 or WO95/02420 published Jan. 26, 1995, incorporated by reference.

Figure 1:
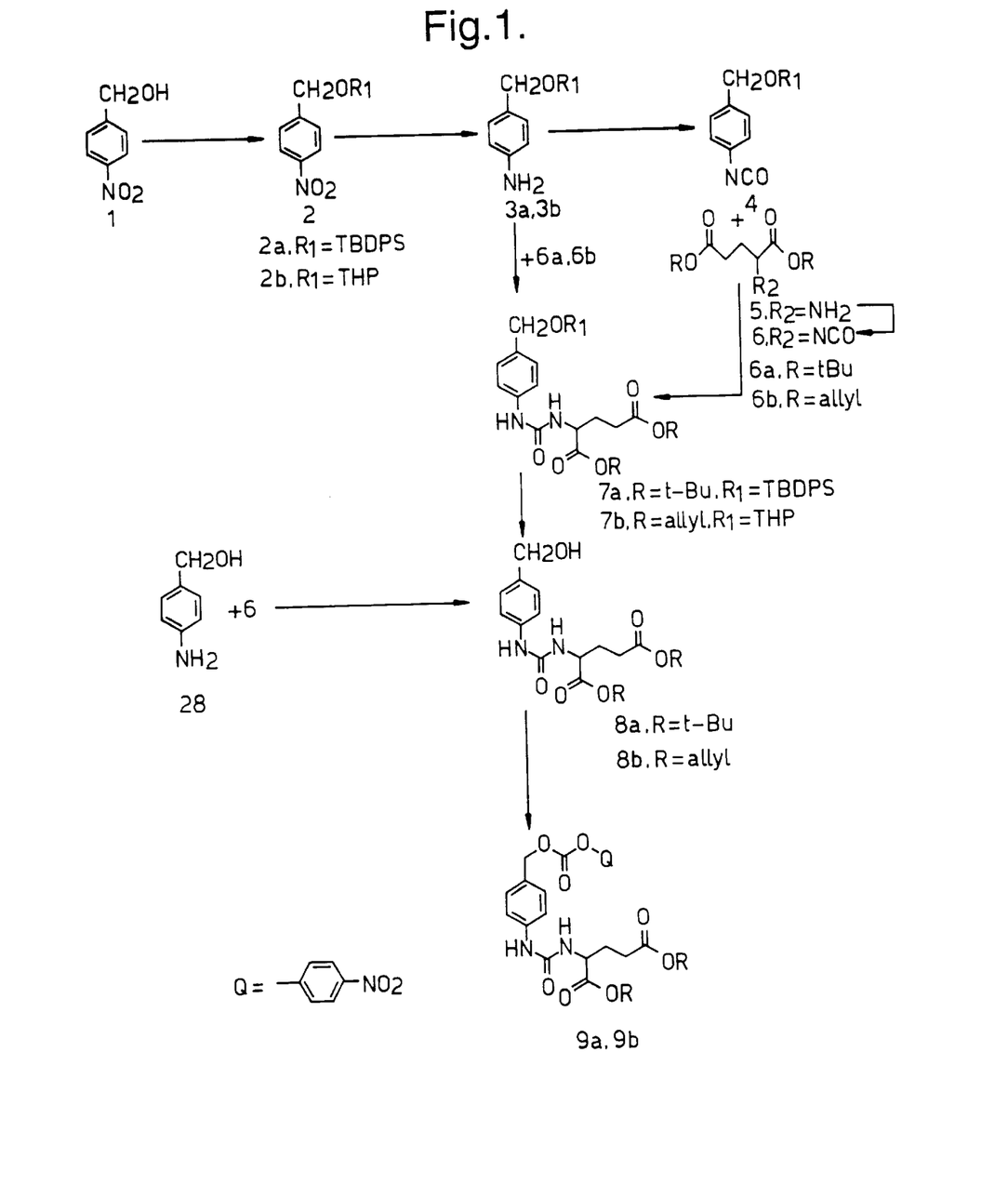
FIG. 1 provides a reaction scheme used to make the compounds described in Example 9.
Figure 2:
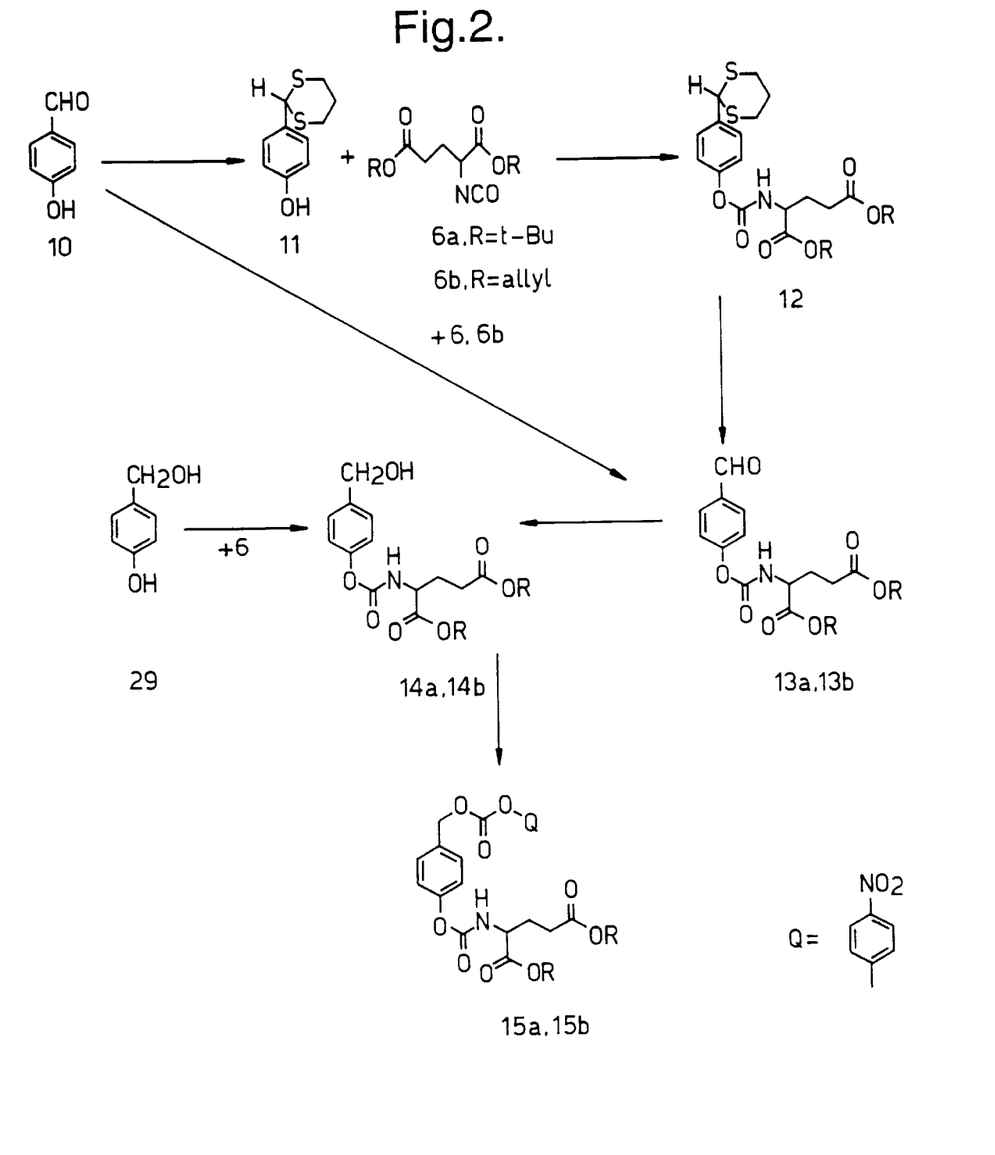
FIG. 2 provides a reaction scheme used to make the compounds described in Example 15.
Figure 3:
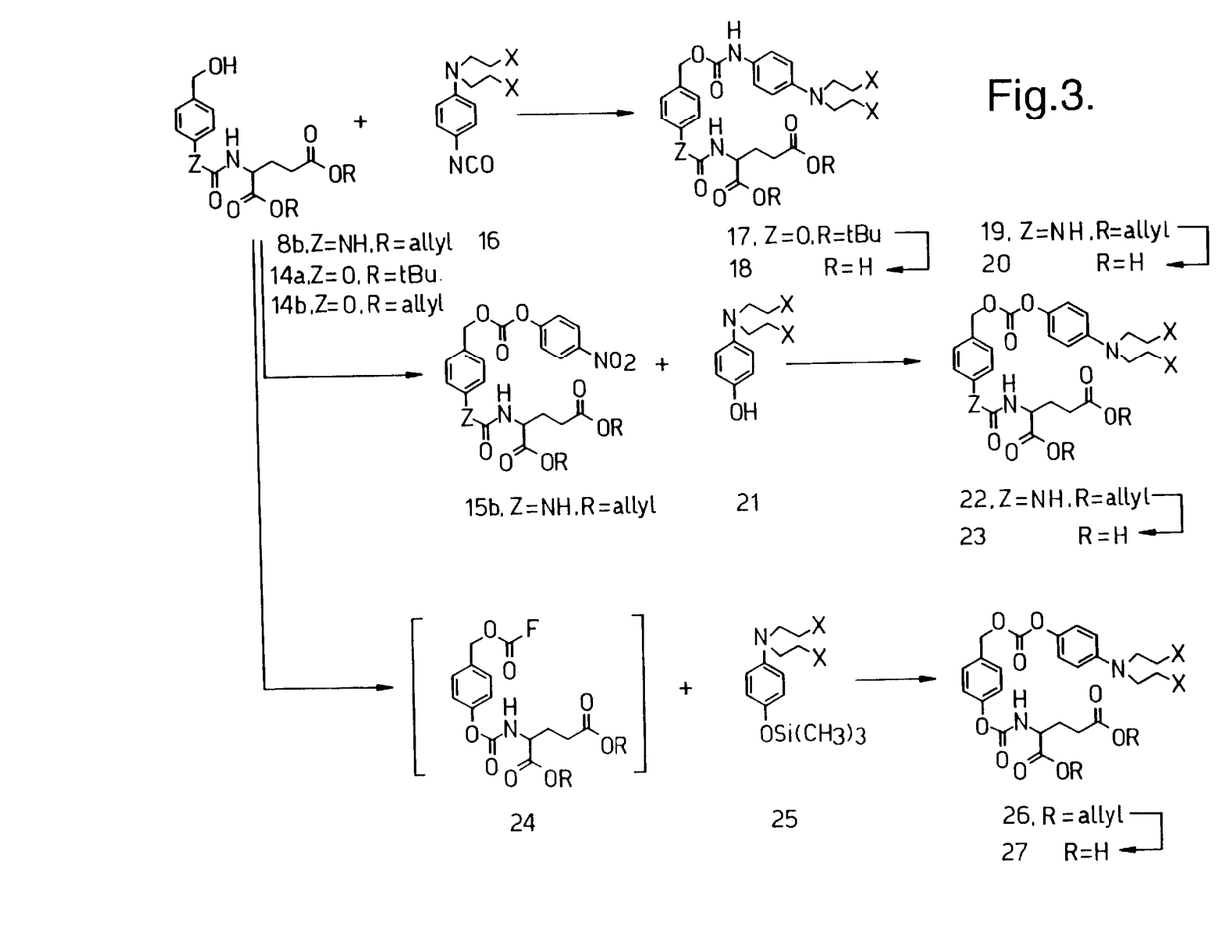
FIG. 3 provides a reaction scheme used to make the compounds of the invention described in examples 1, 2, 3 and 4.

The following Examples illustrate the invention. The numbering of compounds given in the examples is according to that shown in schemes 1–3.

EXAMPLE 1

Diallyl,[(4'-(N,N-bis(2-chloroethyl)amino) phenyloxycarbonvyl-oxy-benzyl-4-carbamoyl-L-glutamate] (22)

Activated linker 15b (0.20 g, 0.37 mmol) and 4-N,N-bis (2-chloroethyl)aminophenol 21 (0.14 g, 0.60 mmol) was dissolved in 10 mL acetonitrile. Then 0.13 g of a strongly basic resin-Amberlyest 27 (OH form) was added and the reaction mixture stirred with the resin for 20 h. The resin was filtered off, and an additional 0.08 g of fresh resin was added. After 30 min of stirring, the second portion of resin was filtered off, and the solvent evaporated. The product, as purified by column chromatograph; (eluent:cyclohexane:AcOEt 2:1), to afford 22 (82 mg, 32%). $^1$H-NMR $\delta_H$: 1.80–2.15 (2m, 2H, $CH_2CH(NH)$—), 2.30–2.45 (m, 2H $CH_2CO_2$-allyl), 3.72 (s, 8H, $N(CH_2CH_2Cl)_2$), 4.30–4.40(m, 1H, CH—G ), 4.55 (d, 2H J=5.41, $CH_2O$ allyl), 4.61 (d, 2H, J=5.31, $CH_2O$ allyl), 5.13 (s, 2H, $PhCH_2$), 5.10–5.40 (m, 4H, $CH_2$= allyl), 5.80–6.00 (m, 2H, CH= allyl), 6.64 (d, 1H. J=8.13 Hz, NH—G), 6.75 (d, 2H, J=9.10 $H_{arom2'+6'}$) 7.04 (d, 2H, $H_{arom3'+5'}$), 7.31 (d, 2H, J=8.55 Hz, $H_{arom2'+6}$) 7.41 (d, 2H, $H_{arom3+5}$), 8.69 (s, 1H,PhNH). MS (FAB), m/z: 636 (M+1, 60), 658 (M+23, 7). anal ($C_{30}H_{35}N_3O_8Cl_2$): calcd C 56.61, H 5.54, N 6.60; found C 56.49, H 5.69, N 6.27.

4'-[N,N-bis(2-chloroethyl)amino] phenyloxycarbonyl-oxy-benzyl-4carbamoyl-L-glutamic acid (23)

To a solution of 22 (100 mg, 0.16 mmol), $PPh_3$ (92 mg, 0.35 mmol) and $Pd(PPh_3)_4$ (16 mg, 0.014 mmol) in $CH_2Cl_2$ (8 mL), acetic acid (1 mL) were added and the mixture stirred for 5 h under argon. The solvent was evaporated, and the residue kept under pump vacuum for 2 h, then dissolved in acetone:AcOEt 1:1. The acetone was evaporated affording 23. $PPh_3$ as a precipitate in AcOEt. The solid was filtered, washed with AcOEt and then dissolved in 50 mL $CHCl_3$ and washed with aqueous citric acid 10% (2×50 mL). The organic layer was collected, $H_2O$ was added and the $CHCl_3$ evaporated yielding 23 (28 mg, 32%) as a precipitate which was filtered from the aqueous solution. $^1$H-NMR $d_H$: 1.80–2.00 (2m, 2H, $CH_2CH(NH)$—), 2.15–2.25 (t, 2H, $CH_2CO_2H$), 3.72 (s, 8H, $N(CH_2CH_2Cl)_2$), 4.10–4.25(m, $PhCH_2$). 6.49 (d, 1H. J=7.34 Hz. NH—G), 6.75 (d, 2H, J=9.10 Hz, $H_{arom2'+6}$) 7.05 (d, 2H, $H_{arom3'+5'}$), 7.29 (d, 2H, J=8.53 Hz, $H_{arom2+6}$), 7.41 (d, 2H, $H_{arom3+5}$), 8.75 (s, 1H,PhNH). MS (FAB). m/z: 556 (M+1, 55), 578 (M+23, 100). Accurate mass ($C_{24}H_{27}N_3O_8Cl_2Na$): calcd. 578.1073; found 578.1070;

EXAMPLE 2

4'-[N,N-bis(2-chloroethyl)amino]phenol-trimethylsilyl ether (25)

Phenol nitrozen mustard 21 (60 mg, 0.26 mmol) and $Me_3SiCN$ (40 μL, 0.3 mmol) were stirred at room temperature without solvent for 30 min; then 10 mL boiling hexane was added to the reaction mixture and the reiiailling solid filtered off. After evaporation of the hexane, 25 (70 mg, 88%) resulted as an oil. $^1$H-NMR $\delta_H$: 0.20 (s, 9H, $Si(CH_3)_3$), 3.55–3.70 (m, 8H, $N(CH_2CH_2Cl)_2$), 6.65 (d, 2H, J=9.30 Hz, $H_{arom3+6}$), 6.73 (d, 2H, $H_{arom\ 3+5}$) MS (FAB), m/z: 304 (M+, 100). Accurate mass: ($C_{13}H_{21}Cl_2NOS$:) calcd. 305.0769; found 305.0765.

diallyl,[(4'-(N,N-bis(2-chloroethyl)amino) phenyloxy-carbonyl-oxy-benzyl-4oxycarbonyl-L-glutamate] (26)

To a stirred solution of 14b (100 mg, 0.26 mmol) in $CH_2Cl_2$ (5 mL) at −78° C., was added phosgene (20% solution in toluene, 150 μL, 0.3 mmol), KF (200 mg, 3.45 mmol) and 18-crown-6 ether (25 μL 0.12 mmol). After 1 h at −78° C. fluoroformate 24 was formed as indicated by IR spectra ($v_{OCOF}$=1827 $cm^{-1}$). Silylated phenol 25 (70 mg, 0.23 mmol) in $CH_2Cl_2$ (3 mL) was added and the solution stirred 1 h more at −78° C. then filtered and the filtrate evaporated. After purification by preparative HPLC (eluent cyclohexane: AcOEt 4:1), 26 (60 mg, 41%) resulted. $^1$H-NMR $\delta_H$: 1.90–2.20 (2m, 2H, $CH_2CH(NH)$—), 2.45–2.60 (m, 2H, $CH_2CO_2$-allyl), 3.72 (s, 8H, $N(CH_2CH_2Cl)_2$), 4.15–4.25(m, 1H, CH—G), 4.57 (d 2H, J=5.40, $CH_2O$ allyl), 4.63 (d, 2H, J=5.28 Hz, $CH_2O$ allyl), 5.23 (s, 2H, $PhCH_2$), 5.15–5.35 (m, 4H, $CH_2$= allyl), 5.85–6.00 (m, 2H, CH= allyl), 6.75 (d, 2H J=9.11 Hz, $H_{arom2'+6'}$), 7.06 (d, 2H, $H_{arom3'+5'}$), 7.14 (d, 2H J=8.51 Hz, $H_{arom3+5}$), 7.41 (d, 2H, $H_{arom2+6}$), 4'-[N,N-bis(2-chloroethyl)amino]phenyl-oxy-carbonyl-oxy-benzyl-4-oxycarbonyl-L-glutamic acid (27)

To a solution of 26 (40 mg, 0.063 mmol), PPh3 (63 mg, 0.24 mmol) and $Pd(PPh_3)_4$ (12 mg, 0.01 mmol) in $CH_2Cl_2$ (3 mL), acetic acid (80 μL) was added and the mixture stirred for 2 h under argon. The solvent was evaporated and the residue dissolved in AcOEt (25 mL), washed with aqueous citric acid 5% (25 mL) and with $H_2O$ (25 mL). The organic layer was dried over $MgSO_4$ and the solvent evaporated. After purification by preparative HPLC (eluent $CH_2Cl_2$:EtOH:AcOH 90:5:5) 27 (8 mg, 25%) resulted. $^1$H-NMR ($CD_3COOD$), $\delta$H: 2.05–2.20 ($CH_2CH(NH)$—), 2.61 (t, 2H, $CH_2CO_2H$), 3.60–3.75 (m, 8H, $N(CH_2CH_2Cl_2$), 4.45–4.55 (m, 1H, CH—G), 5.23 (s, 2H $PhCH_2$), 6.73 (d, 2H, J=9.20 Hz, $H_{arom2'+6'}$), 7.6 (d, 2H, $H_{arom3'+5'}$), 7.19 (d, 2H, J=8.59 Hz, $H_{arom3+5}$)), 7.45 ($\delta$, 2H, $H_{arom2+6}$); MS, (ESI) m/z: 557 (M+1, 3).

EXAMPLE 3 di-t-butyl,[(4'-(N,N-bis(2-chloroethyl)amino) phenylcarbamoyl-oxy-benzyl-4-oxycarbonyl-L-glutamate] (17)

To a solution of, 14a (60 mg 0.15 mmol) in toluene (5 mL) was added isocyanate 16 (0.60 mmol) in toluene (5 mL) and dibutyltin dilaurate (10 μL). The reaction mixture was stirred for 12 h at room temperature. The solid which formed was filtered off and the filtrate evaporated. Purification was achieved by column chromatography (eluent:cyclohexane:AcOEt 3: 1), when product 17 (90 mg, 90%) was obtained as an oil. $^1$H-NMR $\delta_H$.1.41 (s, 9H, t-Bu), 1.42 (s, 9H, t-Bu), 1.65–2.05 (2m, 2H, $CH_2CH(NH)$—), 2.30–2.40 (m, 2H, $CH_2CO_2$-t-Bu), 3.68 (s, 8H, $N(CH_2CH_2Cl)_2$), 3.95–4.15 (m, 1H, CH—G), 5.10 (s, 2H, $PhCH_2$), 6.70 (d,2H, J=8.75 Hz, $H_{arom3'+5'}$), 7.10 (d, 2H, J=8.31 Hz, $H_{arom3+5}$), 7.28 (d, 2H, $H_{arom2'+6'}$), 7.42 (d, 2H, $H_{arom2+6}$), 8.92 (d, 1H, J=7.80 Hz, NH—G), 9.36 (s, 1H, Ph'—NH). MS, m/z (FAB): 667 (M+1, 5), 689 (M+23, 100).

4'-[N,N-bis(2-chloroethyl)amino]phenylcarbamoyl-oxy-benzyl-4-oxycarbonyl-L-glutamic acid (18)

Di-t-butyl ester 17 (90 mg, 0.135 mmol) was dissolved in formic acid (10 mL) and stirred under argon at 12° C. for 24 h. The reaction mixture was lyophilised, the freeze-dried material triturated with $CH_2Cl_2$, the solvent removed and the solid kept in a dessicator 24 h under vacuum to afford 18 (65 mg, 87%). $^1H$-NMR $\delta_H$: 1.75–2.15 (2m, 2H. $CH_2CH$ (NH)—), 2.30–2.50 (m, 2H, $CH_2CO_2H$), 3.68 (s, 8H, $N(CH_2CH_2Cl)_2$), 3.95–4.10 (m, 1H, CH—G), 5.10(s, 2H, $PhCH_2$), 6.70 (d, 2H, J=8.66 Hz, $H_{arom3'+5'5}$), 7.11 (d, 2H, J=8.29, $H_{arom3+5}$), 7.28 (d, 2H, $H_{arom2'+6'}$), 7.42 (d, 2H, $H_{arom2+6}$), 8.07 (d, 1H, J=7.80 Hz, NH—G), 9.36 (s, 1H, Ph'NH). MS, m/z (FAB): 555 (M, 90), 578 (M+23, 100). Accurate mass: calcd: $(C_{24}H_{27}N_3O_8Cl_2Na)$, 578.1073, found: 578.1070.

EXAMPLE 4 diallyl,[(4'-(N,N-bis(2-chloroethyl)amino) phenylcarbamoyl-oxy-benzyl4-carbamoyl-L-glutamate] (19)

A similar procedure as for 17 was used, starting from isocyanate 16 (0.54 mmol) in toluene (5 mL). 8b (0.10 g, 0.27 mmol) dissolved in $CH_2Cl_2$ (5 mL), and dibutyltin dilaurate (10 μL), to yield 19 as a solid. After further recrystallisation from hexane:AcOEt 9:2 19 (0.11 mg. 64%) resulted. $^1H$-NMR $\delta_H$: 1.75–2.15 (2m, 2H, $CH_2CH(NH)$—), 2.35–2.50 (m, 2H, $CH_2CO_2$-Allyl ), 3.68 (s, 8H, $N(CH_2CH_2Cl)_2$), 4.25–4.40(m, 1H, CH—G), 4.55 (d, 2H, J=5.39 Hz, $CH_2O$ allyl), 4.61 (d, 2H, J=5.37 Hz, $CH_2O$ allyl), 5.01 (s, 2H, $PhCH_2$), 5.15–5.35 (m, 4H, $CH_2$= allyl), 5.80–6.05 (m, 2H, CH= allyl), 6.61 (d, 1H, J=7.97 Hz, NH—G), 6.69 (d, 2H, J=8.99 Hz, $H_{arom3'+5'}$) 7.28 (d, 4H, J=7.79 Hz, $H_{arom2+6}+H_{arom2'+6'}$), 7.39 (d, 2H, $H_{arom3+5}$), 8.64 (s, 1H, PhNH), 9.30 (s, 1H, Ph'NH). MS, m/z (FAB): 635 (M+1, 5), 657 (M+23, 5).

4'-[N,N-bis(2-chloroethyl)amino]phenylcarbamoyl-oxy-benzyl-4-carbamoyl-L-glutamic acid (20)

Diallyl ester 19 (40 mg, 0.06 mmol) dissolved in $CH_2Cl_2$ (2 mL) was stirred with $Pd(PPh_3)_4$ (4 mg) and pyrrolidine (15 μL, 0.15 mmol) The reaction mixture was kept under argon for 45 min then diluted with 2 mL toluene. The pyrrolidine salt of the acid 20 precipitated and was recovered by filtration. The free acid was obtained by extracting the precipitate with $CH_2Cl_2$ laqueous citric acid 10%. The organic layer was washed with $H_2O$ and evaporated to give the free acid (20 mg, 60% ) after filtration of the remaining water. $^1H$-NMR $\delta_H$: 1.70–2.05 (2m, 2H, $CH_2CH(NH)$—), 2.20–2.35 (m, 2H, $CH_2CO_2$-allyl), 3.68 (s, 8H, $N(CH_2CH_2Cl)_2$), 4.15–4.30(m, 1H, CH—G), 5.01 (s, 2H, $PhCH_2$), 6.45 (d, 1H, J=7.98 Hz, NH—G),6.69 (d, 2H, J=9.05 Hz, $H_{arom3'+5'}$), 7.27 (d, 4H, J=8.60 Hz, $H_{arom2+6}+H_{arom2'+6'}$), 7.39 (d, $2H_{J=852}$, $H_{arom3'+5'}$), 8.65 (s, 1H, PhNH), 9.30 (s, 1H, Ph'NH). MS (FAB). m/z: 554 (M, 50), 577 (M+23,100). Accurate mass: calcd: $(C_{24}H_{28}N_4O_7Cl_2Na)$ 577.1233, found: 577.1230.

EXAMPLE 5

(4-nitro-benzyl) t-butyl-di-phenyl-silyl ether (2a).

To a stirred solution of 4-nitrobenzyl alcohol (1.00 g, 6.50 mmol) and imidazole (0.97 g, 14.10 mmol) in DMF (10.0 mL), t-butyl-diphenyl-chlorosilane (1.98 g, 1.87 mL, 7.20 mmol) was added over 10 min under nitrogen at room temperature. The reaction mixture was stirred for an additional 5 h, diluted with 75 mL $Et_2O$, washed with $H_2O$ (5 times, 15 mL), dried ($MgSO_4$) and evaporated under vacuum. An oil which crystallised on standing, resulted; yield: 2.54 g. After recrystallisation from EtOH 70%, 2.36 g (93%) of a white soiid is obtained mp 80–81° C. $v_{max}/cm^{-1}$ (film): 2931. 2857 ($CH_2$, asym., sym.), 1521. 1345 ($NO_2$); $^1H$-NMR, $\delta_H$: 1.06(9H, s, t-Bu), 4.92 (2H, s, $CH_2$), 7.42–7.46 (5H, m, Ph), 7.63–7.65 (7H, m, Ph+$H_{arom2+6}$), 8.23, (2H, d, J=8.23 Hz, $H_{arom3+5}$); MS, (EI), (391.54); m/z: 334 (M–t-Bu, 100), 288 (M–t-Bu–$NO_2$, 10), 256 (M–t-Bu–Ph, 20), 199 ($Ph_2SiOH^+$, 100); $C_{23}H_{25}NO_3Si$.

4-nitro-benzyl -2'-tetrahydropyranyl ether(2b).

To a stirred solution of 4-nitrobenzyl alcohol (1.53 g, 10.0 mmol) in $CH_2Cl_2$ (50 mL), 3,4-dihydropyran (1.36 mL 1.26 g, 150 mmol) and pyridinium-p-toluene sulphonate (0.25 g) were added. After 1.5 h the reaction mixture was evaporated to 4–5 mL, AcOEt (25 mL) was added and the solution washed with water (3×50 mL), then brine, dried ($MgSO_4$) and evaporated under vacuum. The product, 2b, (2.46 g, 99%) resulted as an oil. $^1H$-NMR, $\delta_H$: 1.51–1.63 (m, 4H, $2H_4'+2H_5'$), 1.66–1.74 (m, 1H, $2H_3'$) 3.50 (s, 1H, $H_6'$), 3.78 (m, 1H, $H_6'$), 4.62 (d, 1H, J=3.8 Hz, $CH_2$-Ph), 4.72 (m, 1H, $H_2'$), 4.81 (d, 1H, $CH_2$—Ph), 7.62 (d, 2H, J=8.5 Hz, $H_{arom}$), 8.22 (d, 2H, $H_{arom}$); MS, (FAB), (237.52); m/z: 260 ($M^+$+23, 15), 236 (M–1, 45), 136 (4-$NO_2C_6H_5CH_2^+$, 100).

EXAMPLE 6

(4-amino-benzyl) t-butyl-di-phenyl-silyl ether (3a)

To a stirred solution of 2a (5.00 g, 12.80 mmol) in ethanol (100 mL) was added Pd/C 10%(1.50 g) and ammonium fornate (4.60 g) in one portion at 20° C. After 1.5 h the catalyst was removed by filtration, the filtrate concentrated under vacuum and the residue partitioned between EtOAc:$H_2O$. The organic layer was dried ($MgSO_4$) and concentrated to give 3a as an oil yield: 4.24 g (91%) $v_{max}/cm^{-1}$ (film): 3433, 3378 ($NH_2$), 2931, 2857 ($CH_2$, asym. sym.): $^1H$-NMR, $\delta_H$: 1.00 (s, 9H. t-Bu), 4.57 (s, 2H. $CH_2$), 4.98 (s broad, 2H, $NH_2$), 6.52 (d, 2H, J=8.25 Hz, $H_{arom3+5}$), 6.96 (d, 2H, $H_{arom2+6}$), 7.42–7.46 (m, 5H, Ph), 7.62–7.65 (m, 5H, Ph): MS, (EI), (361.56); m/z: 361 ($M^+$, 8), 304 (M–t-Bu, 100), 199 ($Ph_2SiOH^+$, 100); anal $(C_{23}H_{27}NOSi)$, C, H, N.

(4-amino-benzyl)-O-2'-tetrahydropyranyl ether (3b)

A similar method as for 3a was employed using 2b (8.53 g. 35.9 mmol) in ethanol (150 mL), Pd/C 10% (3.50 g) and ammonium formate (12.0 g, 180.0 mmol). An oil (6.40 g, 86%) resulted after work up, which was purified by column chromatography (cycloliexane:AcOEt 1:1): The desired compound eluted first as an oil (2.59 g. 38%). $v_{max}/cm^{-1}$ (film): 3447, 3360 ($NH_2$, sym, asym) 2943, 2870 ($CH_2$, asym., sym.); $^1H$-NMR, $\delta_H$: 1.42–1.53 (m, 4H, $2H_4+2H_5$), 1.55–1.72 (m. 1H. $2H_3$.) 3.45 (s, 1H, $H_6$.), 3.79 (m, 1H, $H_6$.), 4.22 (d, 1H, J=11.1 Hz, $CH_2$—Ph), 4.37 (d, 1H, $CH_2$—Ph), 4.60 (d, 1H, $H_2$.), 5.00 (s, 2H, $NH_2$), 6.52 (d, 2H, J=8.23 Hz, $H_{arom}$), 6.97 (d, 2H, $H_{arom}$); MS, (EI), (207, 27); m/z: 207 ($M^+$, 100), 106 ($H_2NC_6H_4CH_2^+$.100): anal $(C_{12}H_{17}NO_2)$ C. H. N.

EXAMPLE 7 di-t-butyl, (t-butyl-di-phenyl-silyl-O-benzyl)-4-carbamoyl-L-glutamate(7a)

Method A: A suspension was formed by adding 0.31 g (0,43 mL, 3.1 mmol) triethylamine to a solution of di-t-butyl-glutamate hydrochloride (0.46 g, 1.55 mmol) in 7 mL THF. The isocyanate, 4a. (0.60 g, 1.55 mmol) dissolved in 3 mL THF (dry) was added to this at room temperature. After 2 h the precipitate was filtered and the solvent removed under vacuum, giving 0.87 g (87%) of an oil. The product was purified by column chromatography (AcOEt: cyclohexane 2:1) yielding 0.53 g (53%) of pure 7a, as a white solid, mp=89–90° C. $v_{max}$/cm$^{-1}$ (film): 3359 (NH), 2932. 2857 (CH$_2$, asym., sym.), 1729 (C=O, ester), 1670 (C=O, urea). 1154 (C—O, str.): $^1$H-NMR, $\delta_H$: 1.03 (s, 9H, t-Bu), 1.40 (s, 9H, t-Bu-glu). 1.43 (s, 9H, t-Bu-glu). 1.68–2.00 (2m, 2H, CH(NH)CH$_2$), 2.18–2.32 (m, 2H, CH$_2$CO$_2$-t-Bu), 4.08–4.12 (m 1H, CH(NH)CH$_2$), 4.68 (s, 2H, PhCH$_2$), 6.38 (d, 1H, J=8.12 Hz, NH-glu). 7.19 (d, 2H, J=8.41 Hz, H$_{arom3+5}$), 7.32–7.47 (m, 7H, Ph+H$_{arom2+6}$), 7.62–7.70 (m, 5H, Ph), 8.54 (s, 1H, NH-Ph); MS, (EI), (646.90); m/z: 590 (M−t-Bu+1, 2), 534 (M−2t-Bu+2, 5), 478 (M+3t-Bu+3, 100), 199 (Ph$_2$SiOH$^{30}$, 100); anal (C$_{37}$H$_{50}$N$_2$O$_6$Si), C, H, N.

Method B: One pot synthesis of compound 7a: To a solution of di-t-butyl-Qlutamate hydrochloride (4.14 g, 14.0 mmol) and triphosgene (1.39 g, 4.67 mmol) in toluene, cooled at −78° C. 3.90 mL (2.83 g. 28 mmol) triethylamine in 10 mL toluene were added dropwise over 30 min. The reaction was allowed to reach room temperature and was completed by 1 h. To this mixture, a solution containing (4-amino-benzyl)t-butyl-diphenyl-silyl ether 3a (5.00 g, 13.8 mmol) and triethylamine (1.95 mL, 14.0 mmol) was added over 5–10 min. The reaction was completed by 20 h. The reaction mixture was filtered, washed with H$_2$O (200 mL). HCl solution 1% (200 mL). Na$_2$CO$_3$ solution 1% (200 mL), H$_2$O (twice, 200 mL), dried (MgSO$_4$) and evaporated under vacuum, yielding a thick oil. Yield: 9.90 g. (TLC, AcOEt:cyclohexane 3:1). The product was used for deprotection without further purification.

diallyl,(2'-tetrahydropyranyl-O-benzyl)-4-carbamoyl-L-glutamate (7b)

A similar one pot procedure was used. starting from diallyl glutamate-p-toluene-sulphonate (1.08 g, 3.1 mmol), triphosgene (0.30 g, 1.03 mmol) and triethylamine (0.86 mL, 0.63 g, 6.2 mmol) in toluene (20 mL) at −78° C. to prepare the diallyl-L-glutamyl isocyanate 6b. To the reaction mixture 3b (0.52 g, 2.5 mmol) and triethylamine (0.41 mL) in 5 mL toluene was added. An oil resulted (1.17 g) which was separated by preparative HPLC using cyclohexane:AcOEt 1.5:1 as eluent. The desired compound separated as an oil (0.75 g, 65%). $v_{max}$/cm$^{-1}$ (film): 3362 (NH$_2$), 2944, 2871 (CH$_2$, asym., sym.); $^1$H-NMR, $\delta_H$: 1.47–1.50 (m, 4H,2H$_4$+2H$_5$.), 1.60–1.88(m, 3H, 2H$_3$+CH$_2$CH(NH)—), 1.88–2.05 (m, 1H, —CH$_2$CH(NH)—), 2.37–2.45 (m, 2H, CH$_2$CO$_2$A), 3.45 (s, 1H, H$_6$.), 3.80 (m, 1H, H$_6$.), 4.20–4.31 (m, 1H,—CH(NH)—), 4.35 (d, 1H, J=11.55 Hz, CH$_2$—Ph), 4.5–34.63 (m, 5H, CH$_2$—Ph+CH$_2$O allyl), 5.18–5.33 (m, 4H, CH$_2$= allyl), 5.80–6.00 (m, 2H, CH= allyl), 6.60 (d, 1H, J=8.03 Hz, NH—G), 7.20 (d, 2H, J=8.47 Hz, H$_{arom}$), 7.35 (d, 2H, H$_{arom}$), 8.47 (s, 1H, NH—Ph): MS, (EI), (460, 53); anal (C$_{24}$H$_{32}$N$_2$O$_7$), C, H, N.

EXAMPLE 8 di-t-butyl,(4-hydroxybenzyl)carbamoyl-L-glutamate (8a)

Tetra-butylammonium fluoride solution in THF (1M) 20.0 mL (2.5 eq) was added to compound 7a (5.15 g, 8.0 mmol) in 100 mL THF at room temperature. The reaction was finished in 3h (TLC, AcOET: cyclohexane 3:1). The reaction mixture was evaporated under vacuum. The oil thus obtained was dissolved in AcOEt (50 mL), washed with water (3×100 mL), dried (MgSO$_4$) and evaporated again. An oil (5.08 g) was obtained. The deprotected compound, 8a. was purified by column chromatography (AcOEt:cyclohexane 3:1) yielding 1.88 g (58.5%) of an oil which crystallised on standing. Recrystallisation from 60% aqueous MeOH afforded a white solid. Mp: 103–104° C.; $v_{max}$/cm$^{-1}$ (film): 3370 (broad, NH+OH), 2967 (CH$_3$), 2930, 2857 (CH$_2$, asym., sym.), 1716 (C=O, ester), 1678 (C=O, amide), 1153 (C—O, str.): $^1$H-NMR, $\delta_H$: 1.40 (s, 9H, t-Bu), 1.42 (s, 9H, t-Bu), 1.72–2.00 (2m, 2H, CH(NH)CH$_2$), 2.20–2.31 (m, 2H, CH$_2$CO$_2$-t-Bu), 4.10–4.18 (m, 1H, CH(NH)CH$_2$), 4.39 (d, 2H, J=5.36 Hz, CH$_2$), 4.99 (t, 1H, CH$_2$OH), 6.38 (d, 1H, J=8.11 Hz, NH-glu), 7.16 (d, 2H, J=8.35 Hz, H$_{arom3+5}$), 7.31 (d, 2H, H$_{arom2+6}$), 8.50 (s, 1H, NH—Ph); MS, (EI), (408.49); m/z: 408 (M$^+$, 10), 352 (M−t-Bu+1, 4), 296 (M−2t-Bu+2, 14): anal (C$_{21}$H$_{32}$N$_2$O$_6$, C,H,N.

dially,(4-hydroxybenzyl)carbamoyl-L-glutamate (8b)

The intermediate 7b (0.61 g, 1.3 mmol) was hydrolysed at 45° C. in 24.5 mL of a mixture AcOH:THF:H$_2$O 4:2:1 for 3.5 h. (monitored by TLC, eluent. AcOEt:cyclohexane 1:1). The reaction mixture was diluted with 50 mL H$_2$O, extracted with ether (2×25 mL), then with AcOEt (2×30 mL). The pooled organic layers were washed with water (2×30 mL), dried MgSO$_4$ and evaporated to dryness (with addition of toluene, 2×30 mL). An oil iesulted (0.52 g) which was purified by preparative HPLC (cyclohexane:AcOEt 1:2), yielding compound 8b (0.221 g, 45%). $v_{max}$/cm$^{-1}$ (film): 3354 (NH$_2$, OH broad), 1737 (C=O, ester), 1659 (C=O, amide); $^1$H-NMR, $\delta_H$: 1.85–1.93 (m, 1H, CH$_2$CH(NH)—), 2.00–2.05 (m, 1H, —CH$_2$CH(NH)—), 2.46 (t, 2H, J=5.42 Hz, CH$_2$CO$_2$A), 4.26–4.35 (m, 1H, —CH(NH)—), 4.40 (d, 2H, J=5.64 Hz, CH$_2$—Ph), 4.55 (d, 2H, J=5.32 Hz, CH$_2$O allyl), 4.61 (d, 2H, CH$_2$O allyl), 4.98 (t, 1H, OH), 5.17–5.37 (m, 4H, CH$_2$= allyl), 5.85–5.94 (m, 2H, CH= allyl), 6.56 (d, 1H, J=8.03 Hz, NH-G), 7.17 (d, 2H, J=8.48 Hz, H$_{arom}$), 7.32 (d, 2H, H$_{arom}$), 8.52 (s, 1H, NH—Ph): MS, (EI), (376.41): m/z: 399 (M$^+$+23, 35), 377 (M$^+$+1, 100), 359 (M$^+$—H$_2$O, 34), anal (C$_{19}$H$_{24}$N$_2$O$_6$), C,H,N.

EXAMPLE 9 di-t-butyl,[4(4'nitrophenyloxoycarbonyl)oxybenzyl]-carbamoyl-L-glutainate (9a)

To a stirred solution of 8a (0.20 g, 0.49 mmol) in dry THF (10 mL) were added 0.11 g (0.5 mmol) 4-nitrophenyl chloroformate and triethylamine (0.1 mL, 0.6 mmol) at room temperature. The reaction uas complete by 1h. The precipitate formed was filtered and the solution concentrated under vacuum. AcOEt (10 mL) was added, the solution washed with brine (2×10 mL), dried aiind evaporated again, giving an oil (0.28 g). The product was purified by column chromatography (0.16 g, 57%) and repurified by preparative HPLC (0.14 g). $v_{max}$/cm$^{-1}$ (film): 3349 (NH$_2$), 2979, 2932 (CH$_2$, asym., sym.), 1767 (C=O, carbonate), 1716 (C=O, ester), 1652(C=O, amide), 1527, 1349 (NO$_2$); $^1$H-NMR, $\delta_H$: 1,39 (9H, s, t-Bu), 1.42 (9H, s, t-Bu), 1.67–2.05 (2H, 2m, CH$_2$CH(NH)—), 2.20–2.38 (2H, 2m, CH$_2$CO$_2$-t-Bu), 4.08–4.21 (1H, m, CH(NH)—), 4.63 (2H, s, CH$_2$Ph), 6.46 (1H, d, J=7.99 Hz, NH-glu), 7.33 (2H, d, J=8.61 Hz, H$_{arom3+5}$), 7.42 (2H, d, H$_{arom2+6}$), 7.56 (2H, d, J=9.17, H$_{arom3'+5'}$), 8.30 (2H, d, H$_{arom2'+6'}$), 8.68 (1H, s, NH—Ph); MS, (EI), (573,60); anal (C$_{28}$H$_{35}$N$_3$O$_{10}$), C, H, N.

diallyl,[4(4'nitrophenyloxycarbonyl)oxybenzyl]-carbamoyl-L-glutamate (9b)

Starting from 8b (0.19 g, 0.50 mmol), 9b was obtained by a similar procedure and purified by preparative HPLC.

Compound 9b resulted as a white solid (0.132 g, 48.6%). $^1$H-NMR, $\delta_H$: 1.86–1.95 (m, 1H, CH$_2$CH(NH)—), 2.03–2.12 (m, 1H, —CH$_2$CH(NH)—), 2.46 (t, 2H, J=7.40 Hz, CH$_2$CO$_2$A), 4.33–4.48 (m, 1H, —CH(NH)—), 4.55 (d, 2H, J=5.33 Hz, CH$_2$O allyl), 4.61 (d, 2H, CH$_2$O allyl), 5.17–5.38 (m, 4H, CH$_2$= allyl), 5.22 (s, 2H, CH$_2$Ph), 5.87–5.96 (m, 2H, CH= allyl), 6.65 (d, 1H, J=8.26 Hz, NH—G), 7.34 (d, 2H, J=8.67 Hz, H$_{arom}$), 7.43 (d, 2H, H$_{arom}$), 7.56(d, 2H, J=9.14 Hz, H$_{arom}$), 8.3.1 (d, 2H, H$_{arom}$), 8.71 (s, 1H, NH—Ph); MS, (EI), (541, ); m/z: 564 (M$^+$+23, 60), 542 (M$^+$+1, 6); anal (C$_{26}$H$_{27}$N$_3$O$_{10}$):C, H, N; accurate mass: calcd. (C$_{26}$H$_{27}$N$_3$O$_{10}$Na): 564.1594; found 564.1590.

EXAMPLE 10 diallyl,(4-hydroxybenzyl)carbamooyl-L-glutamate (8b)

To a solution of diallyl, glutamyl isocyanate 6b, [prepared from diallyl glutamate-p-toluene sulphonate (10.0 g, 25.0 mmol), triphosgene (2.46 g, 8.3 mmol) and triethylamine (10.5 mL, 75.0 mmol. 3 eq) in 100 mL THF, at −78° C.] was added dropwise 4-aminobenzyl alcohol, 28, (3.0 g, 24.3 mmol) and triethylamine (3.41 mL, 24.3 mmol) in 20 mL toluene, over 10 min at room temperature. The reaction was complete by 15 min. The reaction mixture was filtered, evaporated to dryness and the residue dissolved in 20 mL AcOEt, washed with water (2×20 mL), dried (MgSO$_4$) and re-evaporated. An oil resulted (10,25 g). 2.7 g of the obtained product was submitted to purification by preparative HPLC when 1.52 g (63%) of pure 8b resulted.

EXAMPLE 11 di-t-butyl,{4[2'(1'3'-S,S-dithienyl)phenyl] oxycarbonyl-L-glutamate} (12).

To a solution of di-t-butyl-glutamyl isocyanate 6a (prepared from di-t-butyl-glutamate hydrochloride (1.50 g, 5.0 mmol), triphosgene (0.50 g, 1.66 mmol) and triethylamine (1.40 mL, 28.0 mmol) in 50 mL toluene, at −78° C.), was added 4[2'(1'3'-S,S-dithienyl}phenol, 11 (1.10 g, 5.0 mmol) and triethylamine (0.70 mL). After 12 h, the solid formed was filtered and the solution washed with: NaOH 1% (75 mL), water (2×75 mL), dried (MgSO$_4$) and evaporated. A white solid (2.30 g, 95.8%) was obtained Recrystallisation from aqueous EtOH 50% afforded the pure 12 (1.81 g, 72.7%). $\nu_{max}$/cm$^{-1}$ (film): 3347 (NH$_2$), 2977, 2945 (CH$_2$, asym., sym.), 1728 (C=O, ester); $^1$H-NMR, $\delta_H$: 1,41 (s, 9H, t-Bu), 1.42 (s, 9H, t-Bu). 1.62–1.90 (m, 2H, CH$_2$-5'), 1.90–2.32 (2m. 2H, CH$_2$CH(NH)—), 2.30–2.40 (m, 2H, CH$_2$CO$_2$-t-Bu), 2.86–2.93 (m, 2H, CH$_2$-4' or 6'), 3.09 (t, 2H, J=12.3 Hz, CH$_2$-6' or 4'), 5.41 (s, 1H, H-2'). 7.08 (d, 2H. J=8.50 Hz, H$_{arom3+5}$), 7.43 (d, 2H, H$_{arom2+6}$), 8.12 (d,1H, J=7.81 Hz, NH-Ph); MS, (EI), (497, 67); m/z,: 497 (M$^+$, 2), 451 (M−t−Bu, 2), 359 (M−2t−Bu, 20); Anal.: (C$_{24}$H$_{25}$NO$_6$S$_2$), C, H, N.

di-t-butyl,(4-benzaldehyl)oxycarbonyl-L-glutamate (13a).

To the solution of dithiane 12 (0.50 g, 1.0 mmol) in CHCl$_3$ (10 mL) and THF (5 mL) was added dropwise a solution of Hg(ClO$_4$)$_2$.3H$_2$O (0.91 g, 2.0 mmol) in 5 mL THF. After 5 min the precipitate was filtered and the solution is washed with H$_2$O (2×25 mL), sodium carbonate (25 mL), H$_2$O (2×25 mL), dried (MgSO$_4$) and evaporated. The compound 13a (0.33g, 81%) was obtained as a clear oil. $\nu_{max}$/cm$^{-1}$ (film): 3347 (NH$_2$), 2979, 2934 (CH$_2$, asym. sym.), 1731 (C=O, ester), 1712 (C=O, aldehyde); $^1$H-NMR, $\delta_H$: 1,41 (s, 9H, t-Bu), 1.43 (s, 9H, t-Bu), 1.80–1.87 (m, 1H, CH$_2$CH (NH)—), 1.96–2.02 (m, 1H, CH$_2$CH$_2$(NH)—), 2.32–2.39 (m, 2H, CH$_2$CO$_2$-t-Bu). 3.99–4.04 (m, 1H, CH—G), 7.34 (d, 2H, J=8.39 Hz, H$_{arom3+5)}$, 7.96 (d, 2H, H$_{arom2+6}$)), 8.29 (d, 1H, J=7.72 Hz, NH—Ph), 9.98 (s, 1H, CHO);

di-t-butyl,(4-hydroxybenzl)oxycarbonyl-L-glutamate (14a)

Compound 13a (0.150 g, 0.36 mmol) dissolved in 5.2 mL of a mixture of H$_2$O:AcOH:CH$_3$OH (1:1:1) was reduced with sodium-cyanoborohydride (0.027 g, 0.43 mmol) at room temperature. After 1h, AcOEt (20 mL) was added, the reaction mixture evaporated, the residue dissolved in AcOEt (20 mL), the solution washed with H$_2$O (20 mL), brine (2×20 mL), dried and evaporated to dryness. Compound 14a (0.127 g, 86%) was obtained as an oil. The final purification was achieved by preparative HPLC (cyclohexane:AcOEt, 2:1). $\nu_{max}$/cm$^{-1}$ (film): 3352 (NH$_2$, OH, broad), 2979, 2945 (CH$_2$, asym., sym.), 1728 (C=O, ester), 1712 (C=O, aldehyde); $^1$H-NMR, $\delta_H$: 1,41 (s, 9H, t-Bu), 1.42 (s, 9H, t-Bu), 1.70–1.82 (m, 1H, CH$_2$CH(NH)—), 1.94–1.99 (m, 1H, CH$_2$CH(NH)—), 2.31–2.38 (m, 2H, CH$_2$CO$_2$-t-Bu), 3.97–4.02 (m, 1H, CH—G), 4.48 (d, 2H, J=5.70 Hz, PhCH$_2$OH), 5.15 (t, 1H, OH), 7.03 (d, 2H, J=8.39 Hz, H$_{arom3+5}$), 7.31 (d, 2H, H$_{arom2+6}$), 8.04 (d, 1H, J=7.88 Hz, NH—Ph), 9.98 (s, 1H, CHO); anal: (C$_{21}$H$_{31}$NO$_7$), C, H, N.

EXAMPLE 12 di-t-butyl,(4-benzaldehyl)oxycarbonyl-L-glutamate (13a).

To a solution of di-t-butyl-glutamyl isocyanate 6a [prepared from di-t-butyl-glutamate hydrochloride (0.200 g, 0.67 mmol), triphosgene (0.067 g, 0.22 mmol) and triethylamnine (0.190 mL, 1.35 mmol) as above] in 15 mL CHCl$_3$, were added 4-hydroxybenzaldehyde (0.082 g, 0.67 mmol) and triethylamine (0.190 mL, 1.35 mmol) in 10 mL CHCl$_3$ over 10 min. The reaction was heated under reflux for 2 h, then the solvent was removed under vacuum. The compound was purified by preparative HPLC (eluent:cyclohexane:AcOEt 6:1). Finally a clear oil was obtained (0.197 g, 72%).

EXAMPLE 13 diallyl,(4-hydroxybenzyl)oxycarbonyl-L-glutamate (14b)

A clear solution of diallyl-glutamyl isocyanate 6b [prepared from diallyl-glutamate p-toluene sulphonate (3.28 g, 8.20 mmol), triphosgene (0.81 g, 2.73 mmol) and triethylamine (3.44 mL, 24.6 mmol) in 50 mL THF, at −78° C., according to the procedure described above] was obtained by filtering the reaction mixture at room temperature. 4-hydroxybenzyl alcohol 29 (1.00 g, 8.10 mmol) was dissolved in THF (dry) (10 mL) and 18-crown-6 ether (0.20 mL) and potassium tert-butoxide (0.16 g, 1.4 mmol) were added. To this mixture. the solution of isocyanate 6b was added dropwise at room temperature with vigorous stirring. The reaction was terminated by addition of AcOH (0.5 mL). The reaction mixture was filtered and the solvent removed under vacuum. The residue was dissolved in AcOEt (20 mL), the solution washed with aqueous NaOH 4% (20 mL), with H$_2$O (2×20 mL), dried and evaporated to dryness. Compound 14b (1.62 g, 53%) resulted and was purified by preparative HPLC (eluent cyclohexane:AcOEt 1:1). Finally a clear oil was obtained (0.80 g, 26.5%). $^1$H-NMR. $\delta_H$: 1.90–2.01 (m, 1H, CH$_2$CH(NH)—), 2.05–2.09 (m, 1H, —CH$_2$CH(NH)—), 2.50–2.56 (m, 2H, CH$_2$CO$_2$A), 3.96–4.05 (m, 1H, —CH(NH)—), 4.48 (d, 2H, J=5.67 Hz, PhCH$_2$OH), 4.58 (d, 2H, J=5.26 Hz, CH$_2$O allyl), 4.63 (d, 2H, CH$_2$O allyl), 5.16 (t, 1H, OH), 5.19–5.38 (m, 4H, CH$_2$= allyl), 5.95–5.99 (m, 2H, CH= allyl), 7.04 (d, 2H, J=8.47 Hz, H$_{arom3+5}$), 7.32 (d, 2H, H$_{arom2+6}$), 8.24 (d, 1H, j=7.82 Hz, NH—Ph); MS, (FAB), (377,); m/z: 400 (M$^+$+23, 82), 378 (M$^+$+1, 3); accurate mass (C$_{19}$H$_{23}$NO$_7$Na): calc. 400.1372; found 400.1376.

EXAMPLE 14 di-t-butyl, [4(4'nitrophenyloxycarbonyl)oxybenzil]-oxycarbonyl-L-glutamate (15a)

Activation of linker 14a (1.0 g, 2.7 mmol) was achieved by the same procedure as in Example 9. After purification, an oil resulted (0.64 g, 41%). $v_{max}$/cm$^{-1}$(film): 3367 (NH$_2$), 2980, 2933 (CH$_2$. asym., sym.), 1767 (C=O, carbonate), 1728 (C=O, ester); $^1$H-NMR, $\delta_H$: 1,41 (s, 9H, t-Bu), 1.43 (s, 9H, t-Bu), 1.89–1.94 (m, 1H, CH$_2$CH(NH)—), 1.96–2.03 (m, 1H, CH$_2$CH(NH)—), 2.31–2.37 (m, 2H, CH$_2$CO$_2$-t-Bu), 3.96–4.05 (m, 1H, CH(NH)—), 5.30 (s, 2H CH$_2$Ph), 7.15 (d, 2H, J=8.46 H$_{arom3+5}$), 7.49 (d, 2H, H$_{arom2+6}$), 7.83 (d, 2H, J=9.17 Hz, H$_{arom3'+5'}$) 8.12 (d, 1H, J=7.83 Hz, NH—Ph); 8.31 (d, 2H, H$_{arom2'+6'}$); MS, (FAB), (574, 50); m/z: 597 (M$^+$+23, 12), 575 (M$^+$+1, 4), 519 (M–t-Bu–1, 10), 463 (M–2t-Bu–2, 4);

diallyl,[4(4'nitrophenyloxycarbonyl)oxybenzyl]-oxycarbonyl-L-glutamate (15b)

Starting from 14b (0.4 g, 1.06 mmol), 15b was obtained by a similar procedure. Purification yielded an oil (0.448 g, 75.5%). $^1$H-NMR, $\delta_H$: 1.80–2.01 (m, 1H, CH(NH)CH$_2$—), 2.03–2.09 (m, 1H CH(NH)CH$_2$), 2.50–2.55 (m, 2H, CH$_2$CO$_2$A), 4.16–4.24 (m, 1H, CH(NH)—), 4.59 (d, 2H, J=5.29 Hz, CH$_2$O allyl), 4.63 (d, 2H, CH$_2$O allyl), 5.19–5.38 (m, 4H, CH$_2$= allyl), 5.31 (s, 2H, PhCH$_2$), 5.90–5.98 (m, 2H, CH= allyl), 7.16 (d, 2H, J=8.43 Hz, H$_{arom3+5}$), 7.50 (d, 2H, H$_{arom2+6}$)7.58 (d, 2H, H$_{arom3'+5'}$), 8.11 (d, 2H, H$_{arom2'+6'}$); MS, (FAB), (542, 50); m/z: 563(M$^+$+23, 10), accurate mass: calcd. (C$_{26}$H$_{26}$N$_2$O$_{11}$Na), 565.1434; found 565.1430.

We claim:

1. A compound of the formula (I):

wherein X and Y are independently chlorine, bromine, iodine, a mesyl group CH$_3$ SO$_3$ or a tosyl group OSO$_2$phenyl (wherein phenyl is optionally substituted by 1, 2, 3, 4 or 5 substituents independently selected from C$_{1-4}$alky, halogen, cyano or nitro;

n is an integer from 0 to 4 and each group R$^1$, which may be the same or different when n is greater than 1, is fluorine, chlorine, bromine, iodine, hydroxy, mercapto, amino, nitro, C$_{1-4}$ alkyl optionally containing one double bond or one triple bond, C$_{1-4}$ alkoxy, —CONR$^7$R$^8$ (wherein R$^7$ and R$^8$ are as defined below), —NH(C$_{1-4}$-alkyl), —N (C$_{1-4}$-alkyl)$_2$ or C$_{2-5}$ alkanoyl; or when n is 2 or more and two groups R$^1$ are on adjacent positions on the phenylene ring, 2 adjacent R$^1$ groups together represent a) C4 alkylene optionally having one double bond;
b) C3 alkylene; or
c) —CH=CH—CH=CH—, —CH=CH—CH$_2$—or —CH$_2$—CH=CH— each optionally substituted with 1, 2, 3 or 4 substituents said substituents each independently selected from the group consisting of C$_{1-4}$ alkyl, C$_{1-4}$ alkoxy, halogen, cyano, nitro, C$_{2-5}$ alkanoyl and —CONR$^7$R$^8$ (wherein R$^7$ and R$^8$ are as defined below);

m is an integer from 0 to 4 and R$^2$, which may be the same or different when m is greater than 1, is fluorine, chlorine, bromine, iodine, hydroxy, mercapto, amino, nitro, C$_{1-4}$ alkyl optionally containing one double bond or one triple bond, C$_{1-4}$ alkoxy, —CONR$^7$R$^8$ (wherein R$^7$ and R$^8$ are as defined below), —NH(C$_{1-4}$-alkyl), —N(C$_{1-4}$-alkyl)$_2$ and C$_{2-5}$ alkanoyl; or when n is 2 or more and two groups R$^1$ are on adjacent positions on the phenylene ring, 2 adjacent R$^1$ groups together represent a) C4 alkylene optionally having one double bond;
b) C3 alkylene; or
c) —CH=CH—CH=CH—, —CH=CH—CH$_2$— or —CH$_2$—CH=CH— each optionally substituted with 1, 2, 3 or 4 substituents said substituents each independently selected from the group consisting of C$_{1-4}$, alkyl, C$_{1-4}$ alkoxy, halogen, cyano, nitro, C$_{2-5}$ alkanoyl and —CONR$^7$R$^8$ (wherein R$^7$ and R$^8$ are as defined below);

Z$^1$ and Z$^2$ are each independently —O— or —NH—;

R$^3$ hydrogen, t-butyl or allyl;

Z$^3$ is a group —V—W where V is —CH$_2$—T— in which T is —CH$_2$—, —O—, —S—, —(SO)— or —(SO$_2$)— (provided that when V has sulphur or oxygen as its second atom, W is other than —COOH) and said group V optionally further carrying one or two substituents Q$^1$ and/or Q$^2$ on carbon; wherein Q$^1$ and Q$^2$ each independently represents C$_{1-4}$ alkyl or halogen; or, when Q$^1$ and Q$^2$ are bonded to adjacent carbon atoms, Q$^1$ and Q$^2$ together may additionally represent a C$_3$–C$_4$ alkylene radical optionally substituted with 1, 2, 3 or 4 substituents independently selected from the group consisting of C$_{1-4}$ alkyl and halogen; and W represents
(1) COOH,
(2) —(C=O)—O—R$^6$ wherein R$^6$ represents a C$_{1-6}$ alkyl, C$_{3-6}$ cycloalkyl or aryl (as defined in 3 below) group;
(3) —(C=O)—NR$^7$R$^8$ wherein R$^7$ and R$^8$ each independently represent hydrogen or a C$_{1-6}$ alkyl, C$_{3-6}$ cycloalkyl, aryl, heteroaryl linked to N via carbon or C$_{7-9}$ arkyl group wherein
aryl is phenyl;
heteroaryl is a 5 or 6 membered ring containing 1 to 3 heteroatoms selected from the group consisting of nitrogen and sulphur;
the aryl moiety per se, the heteroaryl moiety and the aryl moiety of the aralkyl group may be substituted on carbon with 1–4 substituents selected from the group consisting of —COOH, —OH, —NH$_2$, —CH$_2$—NH$_2$, —(CH2)$_{1-4}$—COOH, tetrazol-5-yl and —SO$_3$H and the alkyl moiety may optionally carry a methyl group;

(4) —SO$_2$NHR$^9$ wherein R$^9$ is as defined for R$^7$ but may additionally represent —CF$_3$, —CH$_2$CF$_3$ or aryl as defined above;

(5) SO$_3$R$^{10}$ in which R$^{10}$ represents H, C$_{1-6}$ alkyl or C$_{3-6}$ cycloalkyl, (6) PO$_3$R$^{10}$R$^{10}$ (wherein the R$^{10}$ radicals, which may be the same or different, are as herein defined)

(7) a tetrazol-5-yl group;

(8) —CONH—SO$_2$R$^{11}$ in which R$^{11}$ represents
   (a) C$_{3-7}$ cycloalkyl;
   (b) C$_{1-6}$-alkyl optionally substituted with substituents selected from the group consisting of aryl as defined below, C$_{1-4}$-alkyl, CF$_3$ or halogen; and
   (c) perfluoro-C$_{1-6}$ alkyl; wherein
      aryl is phenyl or phenyl having 1–5 substituents wherein the substituents are selected from the group consisting of halogen, —NO$_2$, —CF$_3$, C$_{1-4}$ alkyl, C$_{1-4}$ alkoxy, —NH$_2$, —NHCOCH$_3$, —CONH$_2$, —OCH$_2$COOH, —NH(C$_{1-4}$-alkyl), —N(C$_{1-4}$-alkyl)$_2$, —NHCOOC$_{1-4}$ alkyl, —OH, —COOH, —CN and —COOC$_{1-4}$ alkyl; and (9) —M-Het wherein M represents S, SO or SO$_2$ and Het represents a 5 or 6 membered heterocyclic aromatic ring linked to M via a carbon atom of the aromatic ring, said aromatic ring containing 1, 2, 3 or 4 heteroatoms selected from the group consisting of O, N and S said aromatic ring optionally being substituted on carbon atoms of the ring with 1, 2, 3 or 4 substituents selected from the group consisting of —OH, —SH, —CN, —CF$_3$, NH$_2$ and halogen;

and physiologically acceptable derivatives of the compound of formula (I).

2. A compound according to claim 1 wherein R$_1$ and R$_2$ are each independently selected from hydrogen and fluorine, R$_3$ is hydrogen and Z$^3$ is a group CH$_2$CH$_2$COOH.

3. 4'-[N,N-bis(2-chloroethyl)amino]phenyloxycarbonyloxy-benzyl-4-carbamoyl-L-glutamic acid.

4. 4'-[N,N-bis(2-chloroethyl)amino]phenyloxycarbonyloxy-benzyl-4-oxycarbonyl-L-glutamatic acid.

5. 4'-[N,N-bis(2-chloroethyl)amino]phenylcarbamoyloxy-benzyl-4-oxycarbonyl-L-glutamic acid.

6. 4'[N,N-bis(2chloroethyl)amino]phenylcarbamoyloxy-benzyl-4-carbamoyl-L-glutamic acid.

7. A two component system for use in the control of neoplasia in a human or animal subject which comprises a compound according to claim 1 and a vector or other delivery system capable of selectively infecting tumour cells in said subject, said vector carrying a DNA or RNA sequence encoding an enzyme capable of converting said compound to a nitrogen mustard active against said tumour.

8. A compound of the formula (IV):

where R$^2$, m, Z$^2$, R$^3$ and Z$^3$ are as defined in claim 1, and Q is a leaving group, with the proviso that when R$^2$ is fluorine, chlorine, bromine, iodine, hydroxy, mercapto, amino; nitro, C$_{1-4}$ alkyl, C$_{1-4}$ haloalkyl, C$_{1-4}$ alkoxy, C$_{1-4}$ haloalkoxy, C$_{2-4}$ alkenyl, C$_{2-4}$ alkynyl, and C$_{2-4}$ haloalkenyl, R$^3$ is hydrogen or a C$_{1-6}$alkyl group, and Z$^3$ is a group —CH$_2$CH$_2$COOX$^{10}$ where X$^{10}$ is hydrogen or a group, then Q is not a N-succinimidyloxy group.

9. A process for the production of a compound of formula (I) as defined in claim 1 which comprises reacting a compound of the formula (III):

in which X, Y, R$^1$ and n are as defined for formula (I) and Z$^4$ is —O— or —NH— with a compound of formula (IV)

in which R$^2$, m, Z$^2$, Z$^3$ and R$^3$ are as defined above, and Q is a leaving group or with a compound of formula (V):

(V)

in which $R^2$, m, $Z^2$, $Z^3$ and $R^3$ are as defined above, and recovering the compound of formula (I) produced.

10. A compound of formula (V)

(V)

wherein $R^2$, m, $Z^2$ and $Z^3$ are as defined in claim 1.

* * * * *